Figure 1:
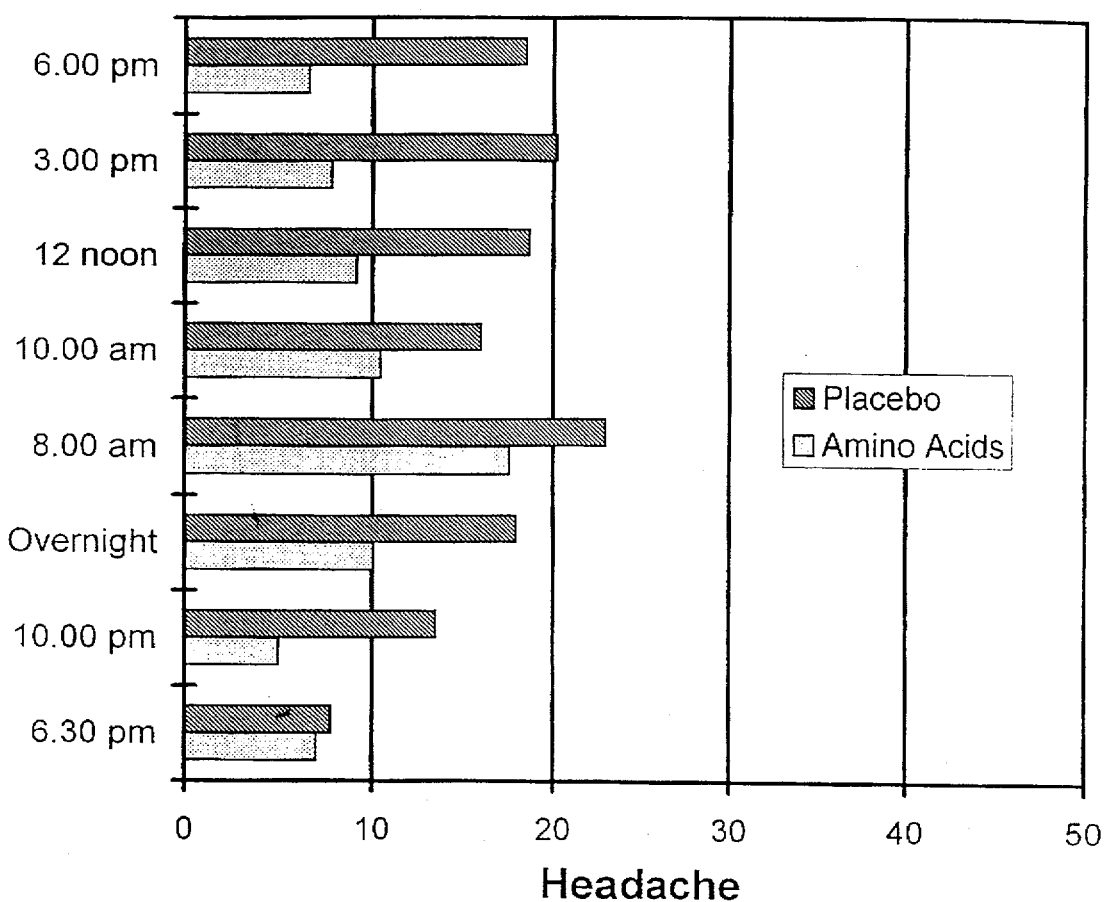

United States Patent [19]

Finnin et al.

[11] Patent Number: 5,712,309
[45] Date of Patent: Jan. 27, 1998

[54] COMPOSITION FOR TREATMENT OF HANGOVERS

[75] Inventors: Barrie Charles Finnin; Timothy Frederick Horewood, both of Victoria, Australia

[73] Assignee: Musashi Pty Ltd., Victoria, Australia

[21] Appl. No.: 592,421

[22] PCT Filed: Aug. 10, 1994

[86] PCT No.: PCT/AU94/00461

§ 371 Date: Apr. 18, 1996

§ 102(e) Date: Apr. 18, 1996

[87] PCT Pub. No.: WO95/04529

PCT Pub. Date: Feb. 16, 1995

[30] Foreign Application Priority Data

Aug. 10, 1993 [AU] Australia ............... PM0450

[51] Int. Cl.$^6$ ........................... A61K 31/195
[52] U.S. Cl. ........................... 514/562
[58] Field of Search ..................... 514/562

[56] References Cited

U.S. PATENT DOCUMENTS

| | | | |
|---|---|---|---|
| 4,357,343 | 11/1982 | Madsen | 514/562 |
| 4,416,898 | 11/1983 | Le Fur | 514/562 |
| 4,792,549 | 12/1988 | Takahashi | 514/400 |
| 4,871,550 | 10/1989 | Millman | 514/562 |
| 5,053,429 | 10/1991 | Hirsch et al. | 514/562 |
| 5,430,064 | 7/1995 | Hirsch et al. | 514/562 |

FOREIGN PATENT DOCUMENTS

| | | | |
|---|---|---|---|
| 0231768 | 8/1987 | European Pat. Off. | |
| 3414491 | 10/1985 | Germany | 514/562 |
| 54-026324 | 2/1979 | Japan . | |
| 59-016817 | 7/1984 | Japan . | |
| 62-029519 | 2/1987 | Japan . | |

OTHER PUBLICATIONS

Derwent Accession No. 84–059245, English Abstract of JP, A2,59016817 (Eisai KK) 28 Jan. 1984 (Jan. 28, 1984).
Derwent Accession No. 87–076349, English Abstract of JP, A2, 62029519 (Daigo Eiyo Kagaku) 7 Feb. 1987 (Feb. 2, 1987).
Derwent Accession No. 26847B, English Abstract of JP, AZ, 54026324 (Morishita Pharm KK) 27 Feb. 1979 (Feb. 27, 1979).

*Primary Examiner*—James H. Reamer
*Attorney, Agent, or Firm*—Ladas & Parry

[57] ABSTRACT

A composition for reducing the symptoms of hangover, including therapeutically effective amounts of L-methionine and L-alanine, or pharmaceutically acceptable salts thereof as active ingredients.

26 Claims, 8 Drawing Sheets

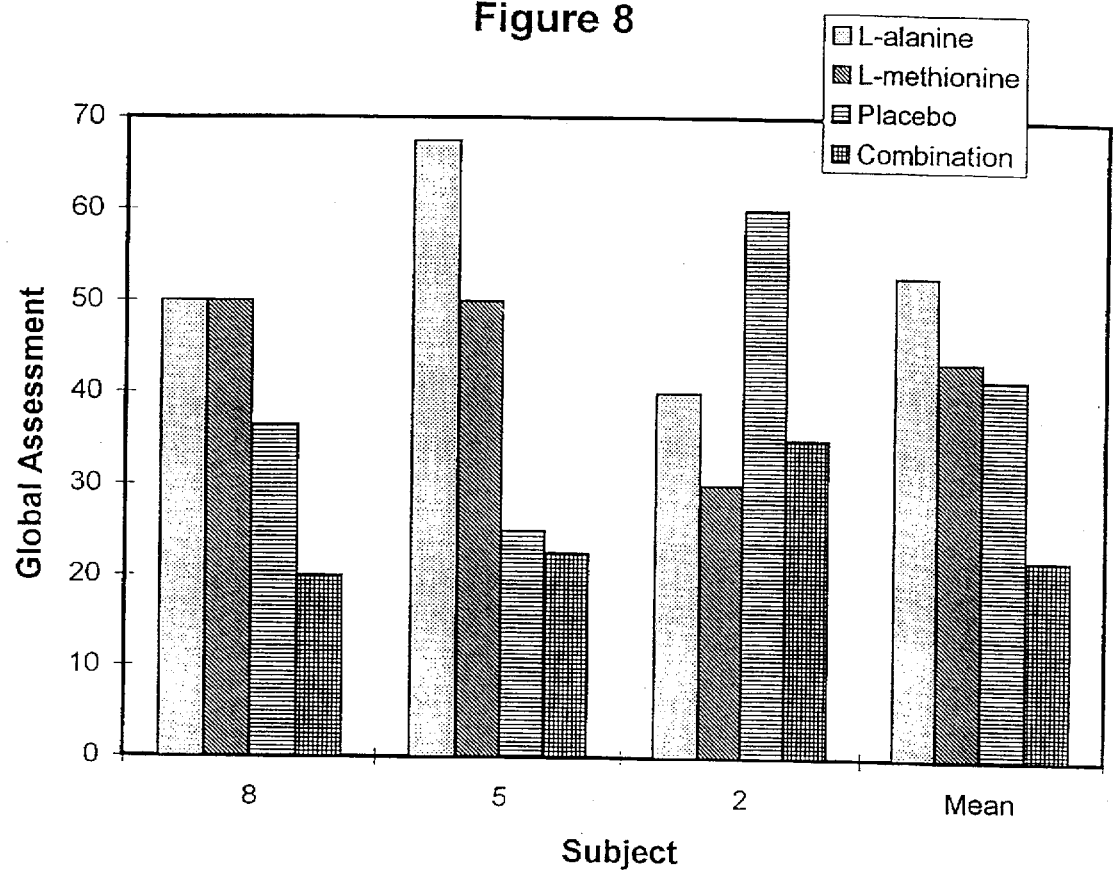

COMPOSITION FOR TREATMENT OF HANGOVERS

FIELD OF THE INVENTION

This invention relates to a composition which may be used to treat hangovers and which may be used to prevent or reduce hangovers. In particular, the invention is directed toward preventing or reducing the symptoms of alcohol-induced hangovers.

BACKGROUND OF THE INVENTION

Hangovers which result from the over indulgence of alcohol are believed to have two basic causes. The first of these is the diuretic effect of ethanol, caused by inhibition of release of endogenous antidiuretic hormone. The result of this diuretic effect is dehydration, which may be overcome by ingestion of large amounts of water following consumption of alcohol.

The second cause of hangovers is the toxic effect of acetaldehyde on the body. The major route for elimination of alcohol is by conversion of ethanol in the liver by alcohol dehydrogenase to produce acetaldehyde. Increase in water consumption has little effect on the elimination of alcohol or acetaldehyde from the body, and hence little effect on this cause of hangover.

The present invention aims to provide a composition which is useful in preventing or reducing the effects of hangovers. It further aims to provide a method of preventing or reducing the effect of hangovers.

In *Alcoholism* 13, 164–71 (1989), Tabakoff, Eriksson and von Wartburg show that methionine ingestion can lower circulating levels of acetaldehyde after ethanol ingestion in mice, rats and humans. The mechanism for this effect is not known, but since liver and serum levels of acetaldehyde are reduced without concurrent reduction in ethanol concentration, it is believed that methionine may increase the clearance of acetaldehyde.

Another amino acid which affects acetaldehyde metabolism is L-alanine. L-alanine has been shown to prevent acute toxicity of acetaldehyde in mice (Fujiwara, Suwa, Yoshizumo, Yamatodani and Wada; *Arukoru Kenkyuto Iakubutsu Ison*, (1988) 23, 58–69).

DESCRIPTION OF THE INVENTION

It has now surprisingly been discovered that by administering a composition containing both L-methionine and L-alanine in conjunction with alcohol consumption, the effects of a hangover may be alleviated or prevented. The effect of this composition is beyond that expected for the combined individual effects of L-methionine and L-alanine, showing a synergy of effect.

Accordingly, the present invention provides a composition for reducing the symptoms of hangover, including therapeutically effective amounts of L-methionine and L-alanine, or pharmaceutically acceptable salts thereof as active ingredients.

It is preferred that the weight ratio of L-methionine to L-alanine is from 1:2 to 2:1 to maximize the effectiveness of the composition.

In a preferred form of the invention, a composition containing substantially equal quantities by weight of L-methionine and L-alanine as active ingredients is prepared. The composition may also contain known pharmaceutically acceptable excipients. In a particularly preferred embodiment, an effervescent composition is prepared containing, in addition to the active ingredients, effervescing agents (for example citric acid anhydrous and sodium bicarbonate), surfactants and wetting agents (for example sodium lauryl sulphate), colouring and flavouring agents and fillers.

The compositions of the invention may be used to treat the effects of a hangover or as a prophylaxis for hangover. The invention also encompasses a method of treatment which includes administration of a therapeutically effective amount of a composition according to the invention to a patient. Administration may be before and/or during and/or after consumption of alcohol, to prevent or reduce the effects of a hangover. Preferably, an effervescent composition containing effective quantities of L-methionine and L-alanine, as well as effervescing agents, and optionally one or more wetting agents, surfactants, colouring agents, flavouring agents or fillers is administered prior to and after consumption of alcohol. In a particularly preferred method, a composition according to the invention is administered at least once prior to alcohol consumption and at least twice after alcohol consumption. A suitable delay is allowed between each administration occurring after alcohol consumption, for example, 6 to 10 hours, or overnight.

The invention will now be discussed in relation to tests conducted by the applicant. Two series of tests were conducted, the first with 8 subjects, the second with 3 subjects. The first test shows the effectiveness of the composition of the invention in alleviating or preventing the symptoms of hangover. The second test shows the synergistic effect of administering L-methionine and L-alanine together, rather than separately. These tests are exemplary only, and are not intended to limit the scope of the invention in any way. The tests are illustrated by the accompanying Figures which show as follows:

TEST I

FIG. 1. The mean rating for headache by eight subjects. The rating was obtained from a visual analog scale where 100 represented a very severe headache, 50 a moderate headache and 25 a slight headache.

Figure 2:
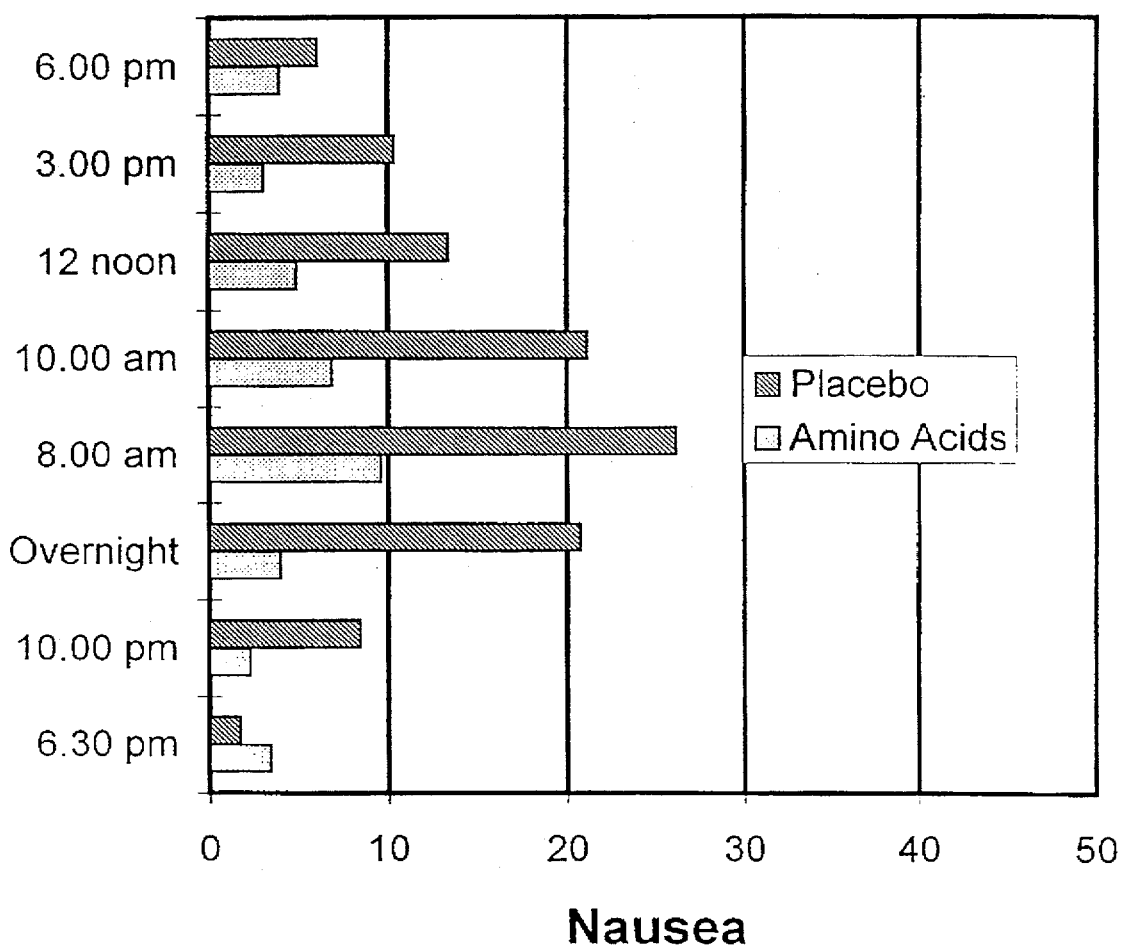

FIG. 2. The mean rating for nausea by eight subjects. The rating was obtained from a visual analog scale where 100 represented very severe nausea, 50 moderate nausea and 25 slight nausea.

Figure 3:
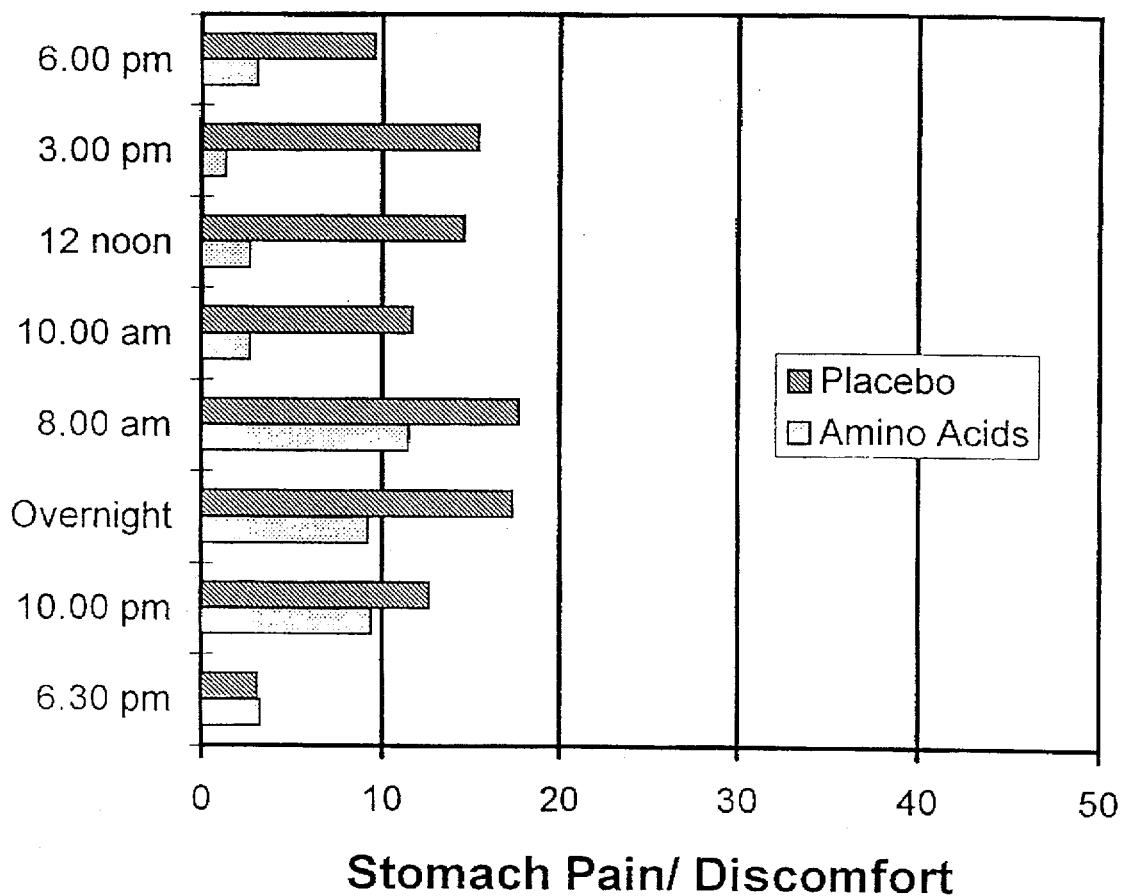

FIG. 3. The mean rating for stomach pain/discomfort by eight subjects. The rating was obtained from a visual analog scale where 100 represented very severe stomach pain/discomfort, 50 moderate stomach pain/discomfort, and 25 slight stomach pain/discomfort.

Figure 4:
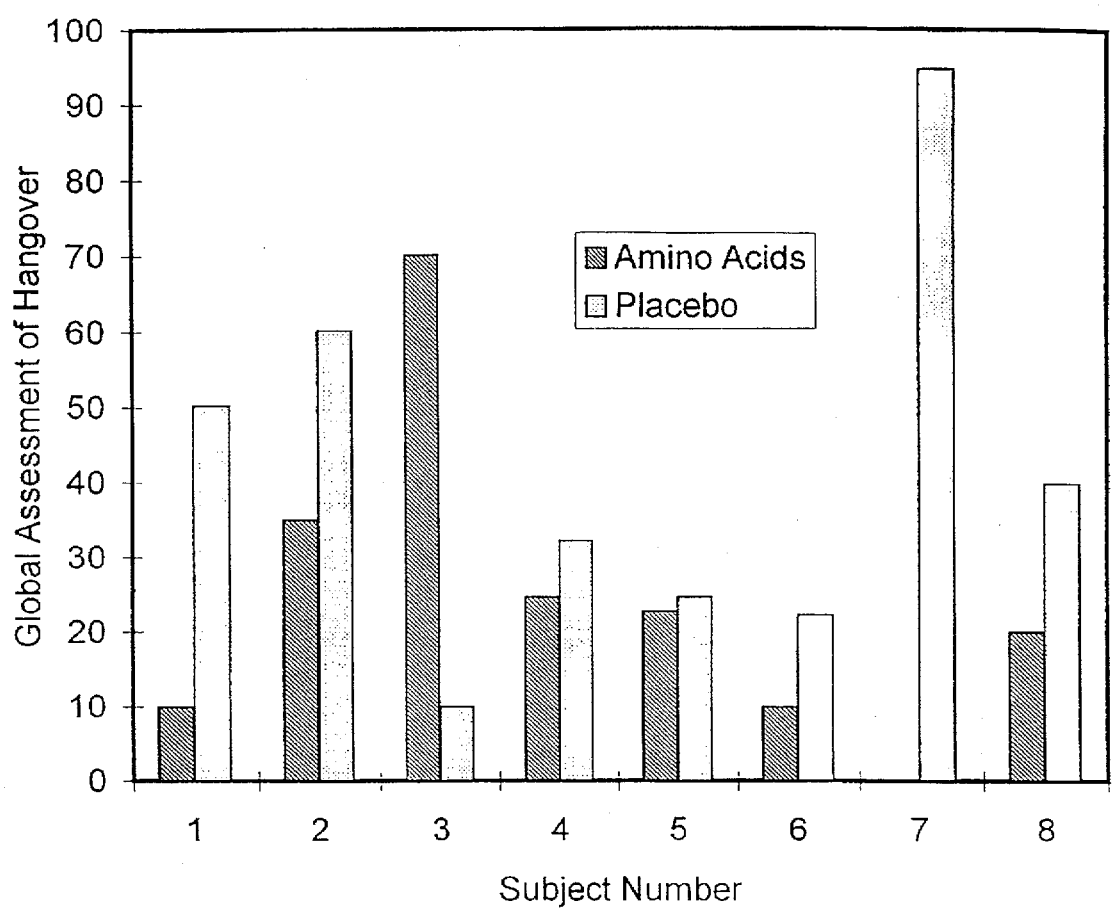

FIG. 4. Global assessment of hangover in the eight subjects. The ratings were obtained from a visual analog scale where 100 represented very severe, 50 moderate and 25 slight. Subject 7 gave a rating of 0 for the global impression of hangover when the amino acids were taken.

TEST II

Figure 5:
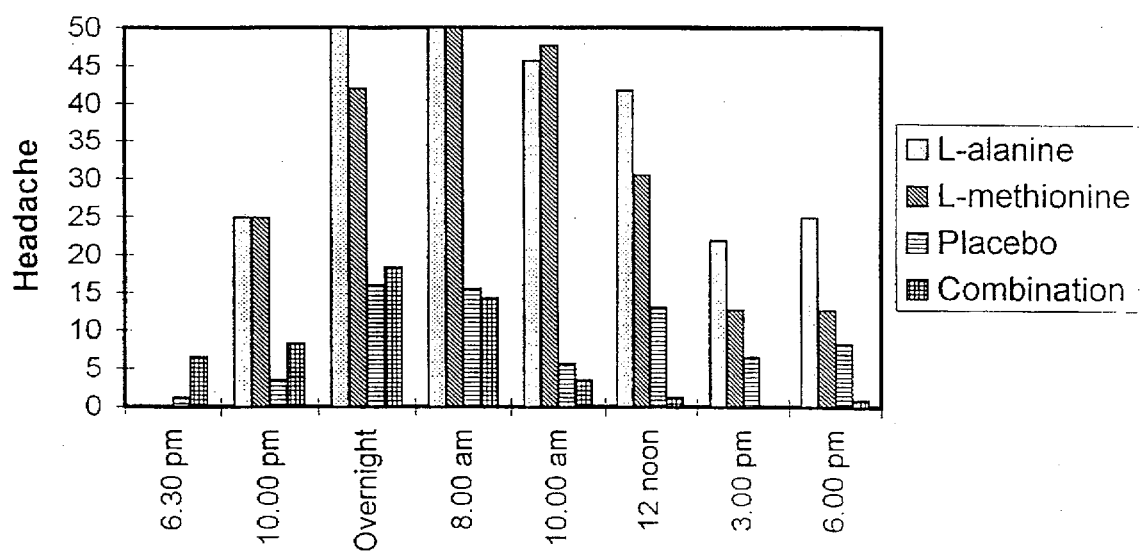

FIG. 5. The mean rating for headache by 3 subjects. The rating was obtained as for FIG. 1.

Figure 6:
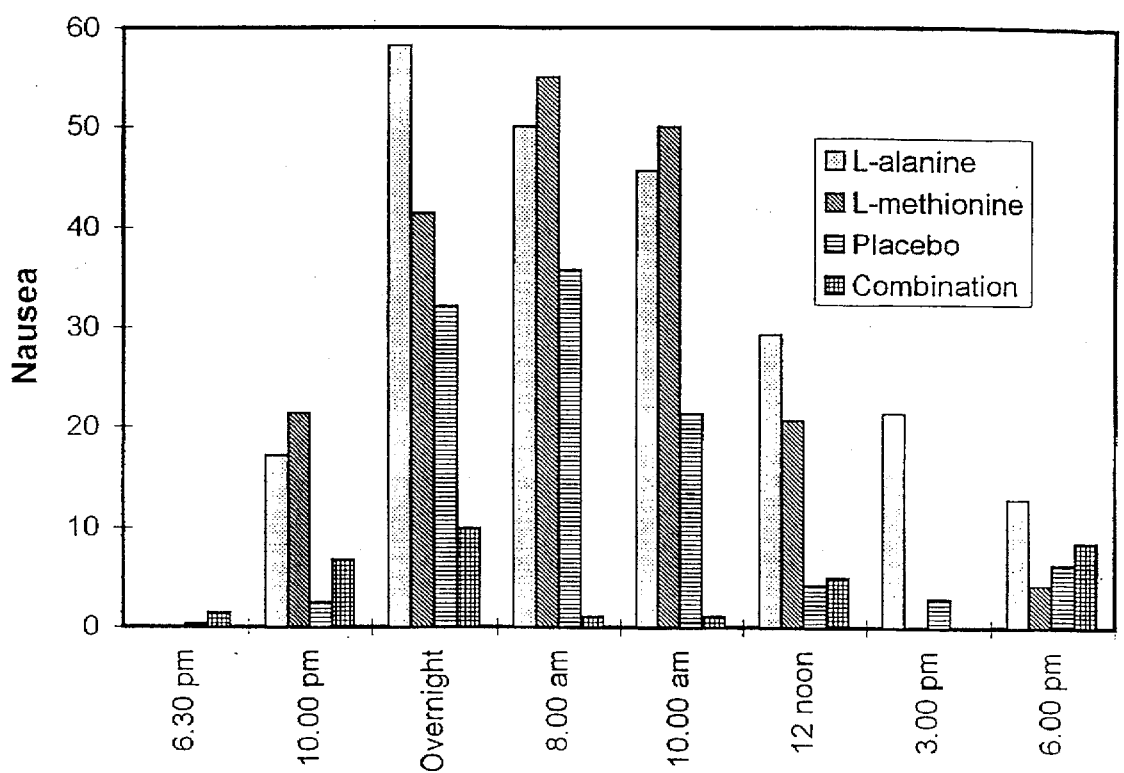

FIG. 6. The mean rating for nausea by 3 subjects. The rating was obtained as for FIG. 2.

Figure 7:
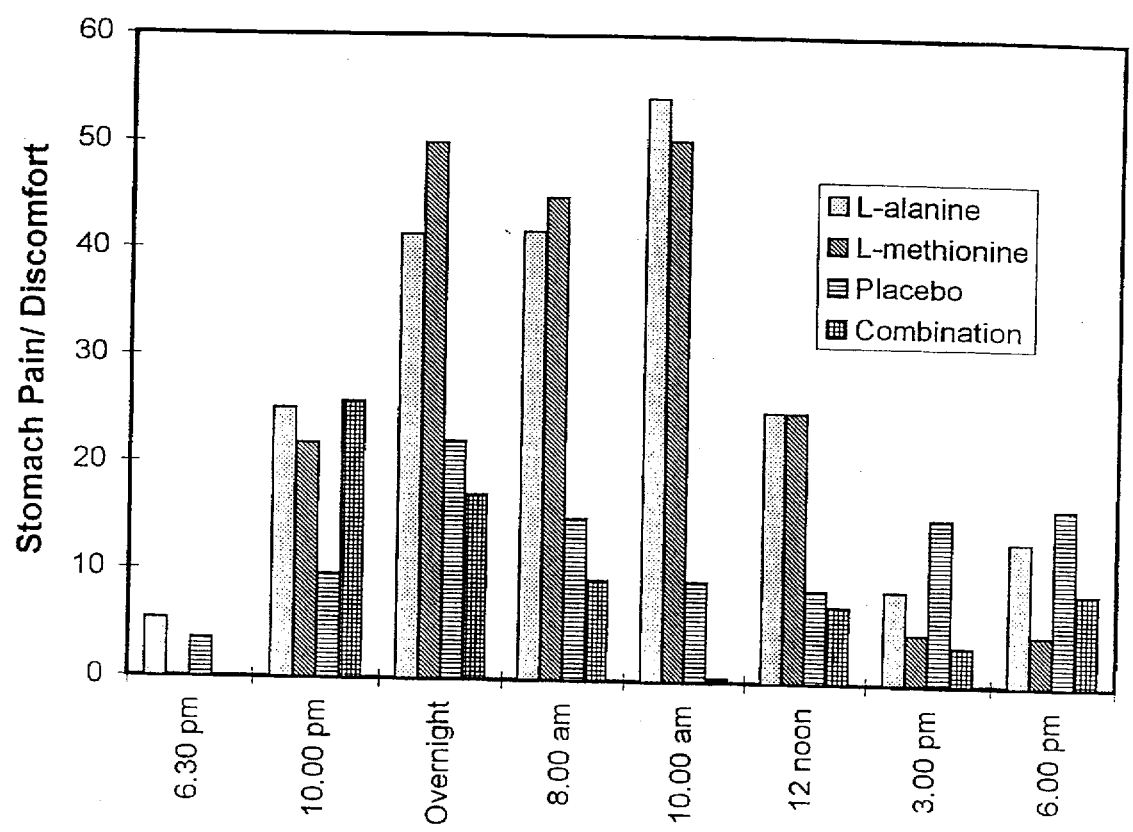

FIG. 7. The mean rating for stomach pain/discomfort by 3 subjects. The rating was obtained as for FIG. 3.

FIG. 8. Globol assesment of hangover in the 3 subjects. The ratings were obtained as for FIG. 4.

TEST I

Because of the difficulty in obtaining an objective method of quantitating "hangover" and because of a perceived psychological component, it was necessary to use a placebo controlled, double blind crossover design for the trial. The trial used six adult males and two adult females as subjects. Subjects were asked to nominate a preferred form of alcohol and a dose which, from previous experience, they would need to imbibe to ensure that they suffered a moderate to severe hangover.

To minimize direct gastric irritation associated with higher alcohol concentrations, the subjects' choice was restricted to drinks having an alcohol content of 20% or less. The alcohol dose is chosen by each subject, as shown in Table 1. The alcohol was consumed over a period of three hours, along with a standard meal (pizza as nominated by each subject), which was repeated on each occasion.

TABLE 1

Proposed Alcohol intake

| Subject | Form | Dose |
| --- | --- | --- |
| 1 | Rum & Coke | 350 ml Rum |
| 2 | Rum & Coke | 350 ml Rum |
| 3 | Scotch & Soda | 350 ml Scotch |
| 4 | Rum & Coke | 350 ml Rum |
| 5 | Rum & Coke | 350 ml Rum |
| 6 | Fosters Lager | 7 × 700 ml Lager |
| 7 | Rum & Coke | 350 ml Rum |
| 8 | Rum & Coke | 350 ml Rum |

Prior to each test, subjects were requested to refrain from alcohol for 48 hours prior to each phase of the trial, and until after the final assessement of hangover on each occasion. Subjects were also requested to refrain from taking amino acid supplements in any form for one week prior to the study and for the duration of the study. Subjects were also requested not to make changes in lifestyle during the study (including diet, smoking and exercise).

The trial involved each subject undergoing two tests with one of preparations A and B on each occasion. Preparation A and B were prepared as follows:

| Preparation A (Active) | |
| --- | --- |
| L-methionine | 2.5 g |
| L-alanine | 2.5 g |
| Citric acid anhydrous | 2.35 g |
| Trucal orange flavour 17-1063 | 0.3 g |
| Sodium lauryl sulphate 1:20 in lactose | 0.01 g |
| Sodium bicarbonate | 2.35 g |
| Total | 10.01 g |

| Preparation B (Placebo) | |
| --- | --- |
| Lactose | 5 g |
| Citric acid anhydrous | 2.35 g |
| Trucal orange flavour 17-1063 | 0.3 g |
| Sodium lauryl sulphate 1:20 in lactose | 0.01 g |
| Sodium bicarbonate | 2.35 g |
| Total | 10.01 g |

All ingredients were ground to a fine powder with a mortar and pestle before mixing.

PROTOCOL
The protocol for each test was as follows:

Day 1

| | |
| --- | --- |
| 6.30 p.m. | Subjects take 10.01 grams of either Preparation A or Preparation B dissolved in 200 ml cold water. |
| 7.00 p.m. | Subjects consume a meal and commence ingestion of alcohol. Alcohol consumption continued up to subject's designated dose over 3 hours. |
| 10.00 p.m. | Subjects take 10.01 grams of preparation as before. Subjects were requested not to drink further alcohol and to note fluid ingestion so as to allow for consistency between tests. |

Day 2

| | |
| --- | --- |
| 8.00 a.m. | Subjects take 10.01 grams of preparation as before. |

The protocol was repeated as above one week later, with each subject taking a different preparation to that taken on the previous occasion. From 6.30 p.m. Day 1 to 6.00 p.m. Day 2, the subjects were required to give subjective evaluations of their physical condition at specified times during the day. Evaluation was by means of a questionnaire.

The questionnaire asked the subjects to record on an analog scale the severity of hangover symptoms, namely: headache, nausea and stomach pain/discomfort. The scales were 10 cm long and were labelled "none", "slight", "moderate", "severe" and "v. severe" at 25 mm intervals. The subjects were instructed to put a mark on the line at a position best describing their current symptoms. The results were quantified by measuring the distance from the left extremity of the line (labelled "none") to the portion marked on the line by the subject. Thus a rating of "v. severe" would have a quantitive value of 100 where "slight" was 25,"moderate" was 50, and "severe" was 75. The subjects were also asked to rate their "global impression of the hangover" at 6.00 p.m. on Day 2 by means of a similar visual analog scale.

RESULTS

The actual alcohol intake of each subject is shown in Table 2.

TABLE 2

The actual alcohol intake by subjects on two occasions

| Subject | Form | Alcoholic Beverage Volume (ml) | Alcohol Dose (ml) |
| --- | --- | --- | --- |
| 1 | Rum & Coke | 360 | 133.5 |
| 2 | Rum & Coke | 360 | 133.5 |
| 3 | Scotch & Soda | 420 | 157.5 |
| 4 | Rum & Coke | 240 | 89 |
| 5 | Rum & Coke | 240 | 89 |
| 6 | Fosters Lager | 4500 | 234 |
| 7 | Rum & Coke | 420 | 155.8 |
| 8 | Rum & Coke | 420 | 155.8 |

A subjective evaluation of each symptom was obtained over the course of the trial. The results for each symptom are as follows:

Headache

The mean results recorded in the questionnaire with respect to headache are summarized in FIG. 1. For both preparations, the peak intensity occurred at 8.00 a.m. on Day 2. At all times the mean rating for headache was higher after the subjects took the placebo. The rating for headache declined from the maximum after ingestion of the active ingredients and was back to pre-drinking levels by 6.00 p.m.

on Day 2, whereas the level of headache had declined only slightly from the maximum by this time where placebo was used.

The normal parametric statistical tests are not applicable with regard to this symptom because of the many zero values recorded. However, if the incidence of headache regardless of the severity is compared (Table 3) it is obvious that more subjects reported suffering from headache after taking the placebo, particularly at the later time points.

Comparison of the frequencies using the G-statistic shows that the incidence of headache was significantly higher at the last three observation times when the placebo was taken rather than when the active ingredients were taken $0.01 < p < 0.025$.

TABLE 3

Number of Subjects Reporting some degree of headache (out of eight subjects).

| Time | Amino Acids | Placebo |
|---|---|---|
| 6.30 pm | 3 | 3 |
| 10.00 pm | 3 | 4 |
| Overnight | 4 | 5 |
| 8.00 am | 5 | 7 |
| 10.00 am | 4 | 6 |
| 12 Noon | 2 | 7* |
| 3.00 pm | 2 | 7* |
| 6.00 pm | 2 | 7* |

*G test $0.01 < p < 0.025$

Nausea

The mean ratings recorded for nausea are shown in FIG. 2. The peak for nausea with both preparations occurred at 8.00 a.m. on Day 2. The level of nausea was much higher at all observation points after drinking when the subjects took placebo. For both preparations the level of nausea declined markedly between 8.00 a.m. and 6.00 p.m. on Day 2.

The mean values in this case are misleading since at 8.00 a.m. Day 2 all but two subjects recorded no nausea when amino acids were taken, compared to only one person not recording nausea when the placebo was taken. The results for each subject at 8.00 a.m. Day 2 are shown in Table 4.

A Mann-Whitney non-parametric test on the data for nausea at 8.00 a.m. Day 2 shows that the difference between the products is significant at the 95% level.

The incidence of nausea at the various time points is shown in Table 4. At three of these points there was significantly less nausea after taking the amino acid preparation then after taking the placebo (G test $p < 0.05$).

TABLE 4

Number of Subjects reporting some degree of Nausea.

| | Amino Acids | Placebo |
|---|---|---|
| 6.30 pm | 2 | 2 |
| 10.00 pm | 1 | 3 |
| Overnight | 3 | 6 |
| 8.00 am | 2 | 7* |
| 10.00 am | 2 | 7* |
| 12 Noon | 3 | 5 |
| 3.00 pm | 1 | 5** |
| 6.00 pm | 2 | 4 |

*G test $0.01 < p < 0.025$
**G test $0.025 < p < 0.05$

Stomach pain/discomfort

The mean ratings for stomach pain/discomfort are shown in FIG. 3. As with other symptoms, the severity of stomach pain/discomfort peaked at 8.00 a.m. Day 2.

The rating declined rapidly to pre-drinking levels when subjects took the amino acid preparation, whereas after the placebo, the level of stomach pain/discomfort remained relatively high for the rest of the observation period. Because many of the subjects showed zero values for many time points, the mean values are misleading and parametric statistics cannot be applied. The individual values for 8.00 a.m. Day 2 are shown in Table 5.

TABLE 5

Subjective evaluation at 8.00 am on the morning after alcohol ingestion.
Subjective Rating

| | Headache | | Nausea | | Stomach Pain/ Discomfort | |
|---|---|---|---|---|---|---|
| Subject | A. Acid | Placebo | A. Acid | Placebo | A. Acid | Placebo |
| 1 | 25 | 67 | 0 | 42 | 0 | 25 |
| 2 | 0 | 10 | 0 | 87 | 25 | 25 |
| 3 | 70 | 25 | 75 | 12 | 40 | 5 |
| 4 | 0 | 25 | 0 | 25 | 25 | 25 |
| 5 | 22 | 25 | 2 | 10 | 2 | 10 |
| 6 | 0 | 0 | 0 | 0 | 0 | 25 |
| 7 | 5 | 50 | 0 | 50 | 0 | 50 |
| 8 | 20 | 10 | 0 | 10 | 0 | 10 |
| Mean | 17.75 | 26.5 | 9.625 | 29.5 | 11.5 | 21.875 |

For explanation of quantitation see protocol.

Another way to view this data is to record the number of subjects showing no signs of a particular symptom at any time point. Results on this basis are presented in Table 6. The number of subjects showing stomach pain/discomfort was higher after placebo than after amino acids at all time points the difference was statistically significant at four of these points (G test $p < 0.05$).

TABLE 6

Number of Subjects Reporting some degree of Stomach pain/discomfort.

| Time | Preparation A. Acid | Placebo |
|---|---|---|
| 6.30 | 1 | 2 |
| 10.00 | 2 | 5 |
| Overnight | 3 | 7* |
| 8.00 am | 4 | 8** |
| 10.00 am | 2 | 4 |
| 12 Noon | 1 | 5 |
| 3.00 pm | 1 | 5 |
| 6.00 pm | 1 | 4 |

*G test $0.025 < p < 0.05$
**G test $0.01 < p < 0.025$

Global Assessment of Hangover by Subjects

Seven of the eight subjects rated the hangover as worse when placebo was taken in comparison to when the amino acid preparation was taken. The results for each subject is shown in FIG. 4.

Objective Evaluations

Two of the eight subjects showed some signs of tremor after taking the amino acids compared with six out of eight showing signs of tremor when the placebo was taken. This difference was statistically significant ($0.025 < p < 0.05$).

Four of the eight subjects showed "normal" skin colour after taking the amino acids compared with three out of eight after the placebo.

The appearance of the eyes were similar in each group.

Conclusions

From the Test I, it appears that the most outstanding effects of the amino acids were the decrease in nausea and the increase rate of resolution of all symptoms. Although standard parametric statistical tests could not be used due to the large number of observations recording a complete absence of a particular effect, non-parametric tests applied showed a highly significant difference between the two treatment groups. For example, the effect on headache is most apparent about 14 hours after alcohol ingestion. While the amino acids appear to have been only slightly effective in preventing headache, they have been very effective in reducing the severity of the headache. A similar pattern of effect was seen with stomach pain/discomfort, where in all but one subject, stomach discomfort was virtually gone by 10.00 a.m. on Day 2 when the amino acids were taken in contrast to the placebo where five subjects were still suffering significant stomach discomfort at this time.

TEST II
SUBJECTS

This trial was performed with three of the subjects that participated in Test I in which the preparation containing a combination of L-alanine with L-methionine was evaluated. The subjects were 2 adult males and 1 adult female.

DOSEFORMS

Subjects took either 2.5 g of L-alanine in powder form or 2.5 g of L-methionine in powder form.

Alcohol Dose and Form

Subjects used the same dose as in Test I.

| Subject | Form | Alcohol Dose |
|---------|-----------|--------------|
| 2 | Rum & Coke | 133.5 ml |
| 5 | Rum & Coke | 89.0 ml |
| 8 | Rum & Coke | 155.8 ml |

PROTOCOL

Subjects were requested to refrain from alcohol for 48 hours prior to the study and until after the completion of the study.

Subjects were requested to refrain from taking amino acid supplements in any form for one week prior to the study and for the duration of the study.

The subjects consumed the dose of alcohol with a meal over a period of approximately three hours.

6.30 pm Subject takes a level spoonful (approximately 2.5 g) of either L-alanine or L-methionine with 200 ml of water. Subjects fill in quesionaire.

7.00 pm Subjects eat and start consuming alcohol.

10.00 pm Subjects take a level spoonful of either L-alanine or L-methionine, as before Subjects complete alcohol ingestion. Subjects fill in questionnaire.

| Next day | |
|----------|---|
| 8.00 am | Subjects take a spoonful of either L-alanine or L-methionine, as before. Subjects fill in questionnaire. |
| 9.00 am | Subjects expected to report to work to try to carry out normal duties. |
| 10.00 am | Subjects fill in questionnaire. |
| 12.00 pm | Subjects fill in questionnaire. |
| 3.00 pm | Subjects fill in questionnaire. |
| 6.00 pm | Subjects fill in questionnaire. |

The protocol was completed for both L-methionine and L-alanine with each subject.

EVALUATION

The evaluation was based on questionnaires.

The questionnaire was filled out at times indicated in the protocol. The subjects were asked to record on an analog scale the severity of headache, nausea and stomach pain/discomfort as in Test I.

The subjects were also asked to rate their "global Impression of the Hangover" at 6.00 pm on the day following the alcohol ingestion.

RESULTS

The results from this study together with the results obtained for the Placebo and the combination of L-alanine and L-methionine for these subjects in Test I are shown in FIGS. 5 to 8.

The rating given by the subjects for headache is shown in FIG. 5. The combination of the amino acids was the only treatment to give a lower intensity of headache than Placebo.

The rating given by the subjects for nausea are shown in FIG. 6. The combination is the only treatment that gave a lower intensity for nausea than Placebo.

The ratings given by the subjects for stomach pain/discomfort are shown in FIG. 7. The combination is the only treatment that gave a lower rating for stomach pain/discomfort than Placebo.

The overall rating of hangover is shown in FIG. 8. The mean ratings show that there is little difference between Placebo and either of the amino acids when given singly. The rating when the combination was given was significantly lower than any of the other treatments.

CONCLUSIONS

In Test II, the amino acids L-alanine and L-methionine were found to have little beneficial effect when taken separately for "hangover". This is in contrast to when the combination is taken together.

It should be realized that various modifications and/or additions may be introduced to the compositions and method of treatment described herein without departing from the spirit or ambit of the invention.

We claim:

1. An amino acid-containing composition for administration to mammals to prevent or treat symptoms of alcohol-induced hangovers consisting essentially of L-methionine and L-alanine or pharmaceutically acceptable salts thereof as active ingredients and a pharmaceutically acceptable solvent, carrier or diluent.

2. A composition according to claim 1 wherein the weight ratio of L-methionine to L-alanine ranges from 1:2 to 2:1.

3. A composition according to claim 1 wherein the composition is adapted for solution or suspension in water.

4. A composition according to claim 1 wherein the composition further comprises one or more of an effervescing agent, a surfactant, coloring agent, flavoring agent and/or a pharmaceutically acceptable filler.

5. A composition according to claim 4 wherein the effervescing agent includes a mixture of citric acid anhydrous and sodium bicarbonate.

6. A composition according to claim 4 wherein the surfactant includes sodium lauryl sulphate.

7. A composition according to claim 1 wherein the composition contains at least 1 g of L-methionine and L-alanine or pharmaceutically acceptable salts thereof.

8. A composition according to claim 1, comprising by weight:

| | |
|---|---|
| 2.5 g | L-methionine |
| 2.5 g | L-alanine |
| 2.35 g | citric acid anhydrous |
| 0.3 g | Trucal orange flavor 17-1063 |
| 0.01 g | Sodium laurel sulphate in 1:20 lactose |
| 2.35 g | Sodium bicarbonate. |

9. A method for preventing and alleviating symptoms of an alcohol-induced hangover, comprising administering orally a prophylactically effective or a therapeutically effective amount of an amino-acid containing composition consisting essentially of L-methionine and L-alanine or pharmaceutically acceptable salts thereof as active ingredients to a person in need thereof.

10. The method according to claim 9 wherein the composition is administered orally before consumption of alcohol.

11. The method according to claim 9 wherein the composition is administered orally before and after consumption of alcohol.

12. The method according to claim 9 wherein the composition is administered after consumption of alcohol.

13. The method according to claim 9 wherein the composition is administered orally once before consumption of alcohol, and twice after consumption of alcohol, wherein the administrations after consumption of alcohol are separated by 6 to 10 hours.

14. An amino acid-containing composition for administration to mammals to prevent or treat symptoms of alcohol induced hangovers comprising L-methionine and L-alanine or pharmaceutically acceptable salts thereof as active ingredients and a pharmaceutically acceptable solvent, carrier or diluent.

15. A composition according to claim 14 wherein the weight ratio of L-methionine to L-alanine ranges from 1:2 to 2:1.

16. A composition according to claim 14 wherein the composition is adapted for solution or suspension in water.

17. A composition according to claim 14 wherein the composition further comprises one or more of an effervescing agent, a surfactant, coloring agent, flavoring agent and/or a pharmaceutically acceptable filler.

18. A composition according to claim 17 wherein the effervescing agent includes a mixture of citric acid anhydrous and sodium bicarbonate.

19. A composition according to claim 18 wherein the surfactant includes sodium lauryl sulphate.

20. A composition according to claim 14 wherein the composition contains at least 1 gram of L-methionine and L-alanine or pharmaceutically acceptable salts thereof.

21. A composition according to claim 14, comprising by weight:

| | |
|---|---|
| 2.5 g | L-methionine |
| 2.5 g | L-alanine |
| 2.35 g | citric acid anhydrous |
| 0.3 g | Trucal orange flavor 17-1063 |
| 0.01 g | Sodium laurel sulphate in 1:20 lactose |
| 2.35 g | Sodium bicarbonate |

22. A method for preventing and alleviating symptoms of alcohol-induced hangover, comprising administering orally a prophylactically effective or a therapeutically effective amount of an amino-acid containing composition comprising L-methionine and L-alanine or pharmaceutically acceptable salts thereof as active ingredients to a person in need thereof.

23. The method according to claim 22 wherein the composition is administered orally before consumption of alcohol.

24. The method according to claim 22 wherein the composition is administered orally before and after consumption of alcohol.

25. The method according to claim 22 wherein the composition is administered after consumption of alcohol.

26. The method according to claim 22 wherein the composition is administered orally once before consumption of alcohol and twice after consumption of alcohol, wherein the administrations after consumption of alcohol are separated by 6 to 10 hours.

* * * * *